(12) United States Patent
Sasaki et al.

(10) Patent No.: US 9,222,923 B2
(45) Date of Patent: Dec. 29, 2015

(54) DATA PROCESSING DEVICE FOR GAS CHROMATOGRAPH AND DATA PROCESSING PROGRAM USED IN SAME

(71) Applicant: HORIBA STEC, CO., LTD., Kyoto-shi, Kyoto (JP)

(72) Inventors: Tomohiro Sasaki, Kyoto (JP); Naoki Wada, Kyoto (JP)

(73) Assignee: HORIBA STEC, CO., LTD., Kyoto (JP)

(*) Notice: Subject to any disclaimer, the term of this patent is extended or adjusted under 35 U.S.C. 154(b) by 7 days.

(21) Appl. No.: 14/197,635

(22) Filed: Mar. 5, 2014

(65) Prior Publication Data

US 2014/0188403 A1    Jul. 3, 2014

Related U.S. Application Data

(63) Continuation of application No. 14/002,201, filed as application No. PCT/JP2012/055475 on Mar. 2, 2012, now abandoned.

(30) Foreign Application Priority Data

Mar. 2, 2011    (JP) .................................. 2011-045783

(51) Int. Cl.
   *G01N 30/86* (2006.01)

(52) U.S. Cl.
   CPC ........ *G01N 30/8675* (2013.01); *G01N 30/8668* (2013.01)

(58) Field of Classification Search
   CPC .................................................. G01N 30/8675
   USPC .......................................................... 702/24
   See application file for complete search history.

(56) References Cited

U.S. PATENT DOCUMENTS

| | | |
|---|---|---|
| 5,827,946 A | 10/1998 | Klee et al. |
| 2006/0194329 A1 | 8/2006 | Ogiwara et al. |

(Continued)

FOREIGN PATENT DOCUMENTS

| | | |
|---|---|---|
| CN | 101876648 | 11/2010 |
| DE | 10324149 | 12/2004 |

(Continued)

OTHER PUBLICATIONS

Castello G et al., "Retention models for programmed gas chromatography", Journal of Chromatography, Elsevier Science Publishers B. V, NL, vol. 1216, No. 10, Mar. 6, 2009, pp. 1607-1623.

(Continued)

*Primary Examiner* — Bryan Bui
(74) *Attorney, Agent, or Firm* — Greenblum & Bernstein, P.L.C.

(57) ABSTRACT

As a data processing device and data processing program for a gas chromatograph, which enable composition, a name, and the like of a registered substance to be extracted from an actually measured retention index by a reverse search, a known RI data storage part that stores a plurality of pieces of known RI data each in which an identifier $G_n$ specific to each registered substance, and retention indices actually measured at a plurality of different temperatures by gas chromatographic analysis on the registered substance indicated by the identifier $G_n$ are paired, and a known RI data conversion part that is configured to convert the retention indices of the registered substance at the plurality of different temperatures to a retention index of the registered substance under a predetermined temperature condition for each of the pieces of known RI data are provided.

10 Claims, 11 Drawing Sheets

(56) References Cited

U.S. PATENT DOCUMENTS

| | | | |
|---|---|---|---|
| 2010/0045300 A1* | 2/2010 | Brothier et al. | ............... 324/468 |
| 2010/0064770 A1 | 3/2010 | Kawana | |
| 2014/0067304 A1 | 3/2014 | Sasaki | |

FOREIGN PATENT DOCUMENTS

| | | |
|---|---|---|
| JP | 02-091565 | 3/1990 |
| JP | 2006-292446 | 10/2006 |
| JP | 2006-292652 | 10/2006 |
| JP | 2009-204618 | 9/2009 |
| WO | 2004/090526 | 10/2004 |

OTHER PUBLICATIONS

Chen B. et al., "The temperature Dependence of Retention Indices in Gas Chromatography", Chromatographia, vol. 25, No. 8, Aug. 1, 1988, pp. 731-734.

Paul G. Boswell et al., "Easy and accurate calculation of programmed temperature gas chromatographic retention times by back-calculation of temperature and hold-up time profiles", Journal of Chromatography A, vol. 1263, Nov. 1, 2012, pp. 179-188.

Extended Eurpean Search Report having mail date of Sep. 15, 2014.

Chinese Office action dated Aug. 5, 2014 .

Wang Zhengfan, "Qualitative and quantitative analysis by chromatography", Chemical industry press, Mar. 31, 2000, pp. 14, along with an English-language translation thereof.

Karoly Heberger et al., "Temperature dependence of Kovats indices in gas-chromatography revisited", Journal of Chromatography A, vol. 973, Dec. 31, 2002, pp. 136.

http://www.nist.gov/mml/chemical_properties/data/electionlibcomp.cfm, "Electron Ionization Library Component of the NIST/EPA/NIH Mass Spectral Library and NIST GC Retention Index Database", Material Measurement Laboratory, Created Feb. 26, 2009, Accessed Mar. 2, 2012.

* cited by examiner $G_1$: $C_{10}H_{13}NO$

| Column type | Active phase | Temperature (°C) | Retention Index |
|---|---|---|---|
| Capillary | DB-5 | 190 | 1482.2 |
| Capillary | DB-5 | 170 | 1461.71 |

$G_2$: $CH_3OH$

| Column type | Active phase | Temperature (°C) | Retention Index |
|---|---|---|---|
| Capillary | DB-5 | 80 | 478 |
| Capillary | DB-5 | 100 | 494 |

● ● ● ● ● ● ● ● ● ● ● ● ● ● ● ● ● ● ● ●

$G_n$: $CH_3COCH_3$

| Cclumn type | Active phase | Temperature (°C) | Retention Index |
|---|---|---|---|
| Capillary | DB-5 | 85 | 589 |
| Capillary | DB-5 | 110 | 635 |

| Column type | Active phase | Temperature (°C) | Retention Index |
|---|---|---|---|
| Capillary | DB-5 | 200 | 1493.2 |

$G_2$: $CH_3OH$

| Column type | Active phase | Temperature (°C) | Retention Index |
|---|---|---|---|
| Capillary | DB-5 | 200 | 913 |

● ● ● ● ● ● ● ● ● ● ● ● ● ● ● ● ● ● ●

$G_n$: $CH_3COCH_3$

| Column type | Active phase | Temperature (°C) | Retention Index |
|---|---|---|---|
| Capillary | DB-5 | 200 | 1234 |

FIG. 5

Candidate set $G_{n1}$
$\{G_{n1}| I_{n}(X)-a \leq I_{n}(G_{n1}) \leq I_{n}(X)+a\}$

| Registered substance | Post-conversion RI at first isothermal analysis temperature $T_{x1}$ |
|---|---|
| $G_1$ | 850.4 |
| $G_2$ | 852.2 |
| $G_3$ | 853.6 |
| $G_4$ | 860.0 |
| $G_5$ | 860.4 |

(a)

$G_4$ included in all candidate sets is outputted as result of identifying unknown sample X Candidate set $G_{n2}$
$\{G_{n2}| I_{n}(X)-a \leq I_{n}(G_{n2}) \leq I_{n}(X)+a\}$

| Registered substance | Post-conversion RI at second isothermal analysis temperature $T_{x2}$ |
|---|---|
| $G_4$ | 853.0 |
| $G_6$ | 843.2 |
| $G_7$ | 850.5 |
| $G_8$ | 860.3 |
| $G_9$ | 862.2 |

DATA PROCESSING DEVICE FOR GAS CHROMATOGRAPH AND DATA PROCESSING PROGRAM USED IN SAME

This application is a continuation of co-pending U.S. application Ser. No. 14/002,201, filed Aug. 29, 2013, which is the U.S. National Stage of International Application No. PCT/JP2012/055475, filed Mar. 2, 2012, which claims priority to Japanese Application No. 2011-045783, filed Mar. 2, 2011. The contents of which are expressly incorporated herein by reference in their entireties.

TECHNICAL FIELD

The present invention relates to a data processing device and data processing program that are intended to convert a value actually measured by gas chromatographic analysis to a value appropriate for comparison or the like.

BACKGROUND ART

A sample qualitative experiment using only gas chromatographic analysis is adapted to inject, for example, a sample desired to be qualified, and a compound as a reference substance, which is expected to be the sample desired to be qualified, into a column with a syringe or the like, and compare respective retention times that are times required for a detector to detect constituents of them. For example, in the case where the respective retention times regarding the constituents are coincident with each other, it can be identified that the sample desired to be qualified is identical to the reference substance.

Meanwhile, a retention time is influenced by a parameter such as a column length or linear velocity of carrier gas, and therefore even if a sample desired to be qualified is coincident with an expected reference substance, in the case where different gas chromatographs or different experimental conditions were used to made measurements, respective retention times are different. That is, in such a case, even in the case of comparing the two retention times with each other, a quality determination cannot be made.

For this reason, in order to be able to prevent the influence of the parameter as described above, and qualify of a substance desired to be qualified, retention indices are compared with each other. To describe more specifically, a retention index is one that is not influenced by many of experimental conditions in gas chromatographic analysis as compared with a measured value such as a retention time, and easily made to serve as a target for comparison at the time of quality determination. For this reason, for example, NIST and the like collect a number of retention indices for each compound, and organize them as a library, and a retention index of a registered substance that is stored in the library and expected to be a sample desired to be qualified, and a retention index that is actually measuring on the sample desired to be qualified are compared with each other to make a quality determination (see Non-patent Literature 1).

Meanwhile, although not being influenced by a column length, linear velocity, or the like, if temperature conditions such as a setting temperature at the time of perform gas chromatographic analysis are different, even retention indices respectively take different values. For this reason, in the case of actually measuring a retention index of a sample desired to be qualified, a retention index of a reference substance expected to be the sample desired to be qualified, which is included in the library, and a temperature condition at the time when the retention index in the library was actually measured are preliminarily obtained, and the temperature condition is set for a gas chromatograph to actually measure the retention index of the sample desired to be qualified.

However, in the case where a sample desired to be qualified is an unknown sample of which composition and the like cannot be expected at all, which registered substance registered in the library should be referred to be unknown, and therefore a temperature condition at the time of performing gas chromatographic analysis cannot be determined in advance. In addition, the temperature condition of the gas chromatographic analysis is appropriately changed for each registered substance, or depending on specifications of a system for the analysis, separation accuracy of a desired constituent, or the like, and therefore retention indices registered in the library are actually measured in various temperature conditions. Accordingly, even in the case of, for the unknown sample, setting a temporary appropriate temperature condition to actually measure a retention index, and using the actually measured value to search the library, a retention index of a registered substance completely irrelevant to the unknown sample is extracted, or other result is obtained, and therefore it is very difficult to identify the unknown sample. In other words, in the currently used retention index library, it is possible to uniquely search for a retention index from a registered substance name; however, in the case of reversely searching a registered substance name or the like from a retention index, a plurality of registered substances are outputted, or in some cases, nothing is outputted because a coincident retention index is not present in the first place. Accordingly, it is considered that even in the case of identifying the unknown sample only by the gas chromatographic analysis, the number of uncertainties is large, and therefore certain identification cannot be made. As evidence of this, for identification of an unknown sample of which identity cannot be expected at all, not only the gas chromatographic analysis, but other analysis such as mass analysis like GC/MS analysis or the like is also typically performed together.

In addition, as a way to handle the case where a temperature condition in the gas chromatographic analysis is different, as disclosed in Patent Literature 1, converting a measured retention time to a retention time, which is registered in the library and under a temperature condition under which the retention time was measured, to make a quality determination is described; however, a method for converting some retention index to a retention index under a predetermined temperature condition is not described as expected. That is, up to now, a method that can qualify an unknown sample even in the case where a parameter such as a temperature condition or linear velocity is different has not been known.

CITATION LIST

Patent Literature

Patent Literature 1: JP-A02-91565

Non Patent Literature

Non Patent Literature 1: http://www.nist.gov/mml/chemical_properties/data/electionlibcomp.cfm

SUMMARY OF INVENTION

Technical Problem

The present invention provides a data processing device and data processing program for a gas chromatograph that enables getting out of a conventional wrong impression that an unknown sample cannot be identified only with a retention index obtained by gas chromatographic analysis as described above, and extraction of composition, name, and the like of a registered substance from an actually measured retention index by a reverse search.

Solution to Problem

That is, a data processing device for a gas chromatograph according to the present invention is provided with a known RI data conversion part that is configured to receive pieces of known RI data indicating retention indices respectively at a plurality of mutually different temperatures, the retention indices being related with an identifier specific to some registered substance, and convert from the retention indices of the registered substance at the plurality of different temperatures to a retention index of the registered substance under a predetermined temperature condition.

That is, the present invention is based on findings as a result of intensive examination by the present inventors that if there are retention indices at a plurality of different temperatures, it is possible to convert to a retention index under a predetermined temperature condition that is a condition other than temperature conditions under which the retention indices were actually measured. Such findings have been made only by getting out of a wrong impression that an unknown sample cannot be identified only by gas chromatographic analysis, and it is necessary to combine with other analysis, as well as setting a technical issue in which a temperature condition-related problem about a retention index should be examined.

Such a data processing device for a gas chromatograph converts to a retention index under a desired temperature condition if there are a plurality of retention indices actually measured for each registered substance, and therefore it is not necessary to, when gas chromatographic analysis is performed on an unknown sample to actually measure a retention index, preliminarily set a temperature condition so as to enable comparison as before. That is, even in the case of performing an experiment with making a free temperature condition setting for each gas chromatograph used, retention indices can be compared with each other, and, for example, even in the case of performing a reverse search from a retention index, a unique result can be outputted, so that a registered substance corresponding to an unknown sample can be identified with high accuracy.

As a specific configuration for, on the basis of a retention index, easily identifying what registered substance an unknown sample is, it is only necessary that the data processing device for a gas chromatograph is one further provided with: a known RI data storage part that stores known RI data on each of a plurality of registered substance; a post-conversion RI data storage part that stores retention indices of at least of registered substances with relating corresponding specific identifiers to the retention indices, the retention indices being converted by the known RI data conversion part; a receiving part that receives the predetermined temperature condition, and a value related to a retention index actually measured on an unknown sample by gas chromatographic analysis using the predetermined temperature condition; and a search part that extracts, from among pieces of post-conversion RI data stored in the post-conversion RI data storage part, post-conversion RI data including a retention index of which a value is coincident with or substantially equal to the value of the retention index of the unknown sample under the predetermined temperature condition, the retention index of the unknown sample being received by the receiving part, and outputs an identifier corresponding to the extracted retention index.

Specific configurations of the known RI data conversion part that can make the number of known retention indices to be used smaller than that in an after-mentioned conversion method that requires retention indices at three different temperatures, and is intended to, as compared with the case of making an actual measurement, almost prevent the occurrence of an error to convert to a retention index under a predetermined temperature condition include one in which the predetermined temperature condition is a condition including an isothermal analysis temperature that is appropriately set when gas chromatographic analysis is performed as isothermal analysis; and the known RI data conversion part is configured to, on a basis of retention indices of the registered substance at a first temperature and a second temperature that are two different temperatures, and adjusted retention times of a reference substance at the first temperature, the second temperature, and the isothermal analysis temperature, converts to a retention index of the registered substance at the isothermal analysis temperature. If so, two different retention indices are only required for one registered substance, and even in an existing retention index library, the number of registered substances of which retention indices measured at two or more different temperatures are registered is predominantly larger than the number of registered substances of which as many as three retention indices are registered, so that a database having a larger number of reference objects can be prepared. That is, it is possible to increase the number of search objects, and therefore the possibility of being able to qualify an unknown sample can be further increased.

As a configuration of the known RI data conversion part that is intended to, when converting from retention indices at two different temperatures to a retention index under a predetermined temperature condition, smoothly perform the sequence of converting from a retention index at some temperature to an adjusted retention time at the some temperature for each registered substance, from which calculating an adjusted retention time under the predetermined temperature condition, and then returning the adjusted retention time to the retention index under the predetermined temperature condition, and thereby easily perform the retention index conversion, it is only necessary that the known RI data conversion part is provided with: a known temperature RT conversion part that, on a basis of retention times of the reference substance at the first temperature and the second temperature, converts from the retention indices of the registered substance at the first temperature and the second temperature to adjusted retention times of the registered substance at the first temperature and the second temperature; an isothermal analysis temperature RT calculation part that, on a basis of a linear relationship between reciprocals of the first temperature and the second temperature, and logarithms of the adjusted retention times of the registered substance, the adjusted retention times corresponding to the first and second temperatures, calculates an adjusted retention time of the registered substance at the isothermal analysis temperature; and an RI calculation part that, on a basis of the adjusted retention time of the registered substance at the isothermal analysis temperature, and the adjusted retention time of the reference substance at the isothermal analysis temperature, calculates the retention index of the registered substance at the isothermal analysis temperature.

For example, in order to configure known RI data that, without preparing an adjusted retention time or the like of a reference substance, enables a retention index to be converted, it is only necessary that the predetermined temperature condition is a condition including an isothermal analysis temperature that is appropriately set when gas chromatographic analysis is performed as isothermal analysis, and the known RI data conversion part is further provided with: an RI temperature function identifying part that, on a basis of retention indices of the registered substance at a first temperature, a second temperature, and a third temperature that are three different temperatures, identifies three constants of a conversion expression that is a function of temperature and given by an expression below; and a temperature substitution operating part that substitutes the isothermal analysis temperature into the conversion expression identified by the RI temperature function identifying part to calculate a retention index of the registered substance at the isothermal analysis temperature.

$$I = A + \frac{B}{T} + C\ln T \qquad \text{[Expression 1]}$$

Here, I: the retention index, T: temperature, and A, B, and C: the constants identified by measured values of retention indices of each registered substance.

In order to be able to convert a retention index even in the case where the predetermined temperature condition is not the isothermal condition but a temperature rising condition, it is only necessary that the predetermined temperature condition is a condition including a temperature rising condition including: a temperature rising rate that is appropriately set when gas chromatographic analysis is performed as temperature rising analysis; and an initial setting temperature, and the known RI data conversion part is provided with: a distribution coefficient function identifying part that, on a basis of retention indices of the registered substance at a first temperature and a second temperature that are two different temperatures, identifies a distribution coefficient of the registered substance as a function of temperature; a temperature rising condition RT calculation part that, on a basis of the distribution coefficient and a column length of a gas chromatograph, calculates an adjusted retention time of the registered substance under the temperature rising condition; and a temperature rising condition RI calculation part that, on a basis of the adjusted retention time of the registered substance under the temperature rising condition, and an adjusted retention time of a reference substance under the temperature rising condition, calculates a retention index of the registered substance under the temperature rising condition.

In order to minimize a load used for the known RI data conversion part to perform conversion, and also prevent unknown sample identifying accuracy from falling, it is only necessary that the known RI data conversion part is configured to convert, from among the retention indices of the registered substance at the plurality of different temperatures, the retention indices being stored in the RI data storage part, a retention index having a value within a predetermined range with respect to the value of the retention index of the unknown sample, the value being received by the receiving part, to the retention index of the registered substance under the predetermined temperature condition.

In order to further improve accuracy at the time of, from retention indices of an unknown sample, which have been actually measured under a plurality of different measurement conditions, qualify a corresponding substance, it is only necessary that the data processing device for a gas chromatograph is further provided with: a post-conversion RI data storage part that stores retention indices of at least of registered substances with relating corresponding specific identifiers to the retention indices, the retention indices being converted by the known RI data conversion part; a receiving part that receives a plurality of combinations each including values respectively related to the predetermined temperature condition and a retention index actually measured on an unknown sample by gas chromatographic analysis using the predetermined temperature condition; and a search part that extracts, from among pieces of post-conversion RI data stored in the post-conversion RI data storage part, a plurality of identifiers respectively having retention indices that are within a predetermined range with respect to the value of the retention index of the unknown sample under the predetermined temperature condition to prepare candidate sets, the retention index of the unknown sample being received by the receiving part, and outputs an identifier common to the respective candidate sets prepared on a basis of the respective combinations each including the predetermined temperature condition and the retention index.

In the case where a data processing program for a gas chromatograph instructs a computer to be provided with a function as a known RI data conversion part that is configured to receive pieces of known RI data indicating retention indices respectively at a plurality of mutually different temperatures, the retention indices being related with an identifier specific to some registered substance, and convert from the retention indices of the registered substance at the plurality of different temperatures to a retention index of the registered substance under a predetermined temperature condition, only by installing the program in a data processing device of an existing gas chromatographic analysis system, an unknown sample can be identified only by gas chromatographic analysis.

Further, in the case where a data processing method for a gas chromatograph is provided with: a receiving step of receiving retention indices respectively at a plurality of mutually different temperatures, the retention indices being related with an identifier specific to each registered substance; and a known RI data conversion step of converting from the retention indices of the registered substance at the plurality of different temperatures to a retention index of the registered substance under a predetermined temperature condition, and a database for a gas chromatograph is provided with a post-conversion RI data storage part that stores a retention index of each registered substance, the retention index being converted by the data processing method for a gas chromatograph, a retention index meeting an experimental condition of gas chromatographic analysis can be easily prepared.

Advantageous Effects of Invention

As described, according to the present invention, on the basis of the knowledge found as a result of intensive examination by the present inventors that if there are retention indices at a plurality of different temperatures, the conversion to a retention index under a desired predetermined temperature condition can be performed, for example, a library or the like of retention indices that have already been collected and have measured under non-uniform temperature conditions can be standardized. This enables an unknown sample to be identified only by gas chromatographic analysis alone, which has been believed to be very difficult.

BRIEF DESCRIPTION OF DRAWINGS

FIG. 4 is a schematic diagram illustrating an outline of data stored in a known RI data storage part.

FIG. 5 is a schematic diagram illustrating an outline of data stored in a post-conversion RI data storage part.

FIG. 11 is a schematic diagram illustrating an example of candidate sets extracted by a search part and an identification result in the fourth embodiment.

REFERENCE SIGNS LIST

Figure 1:
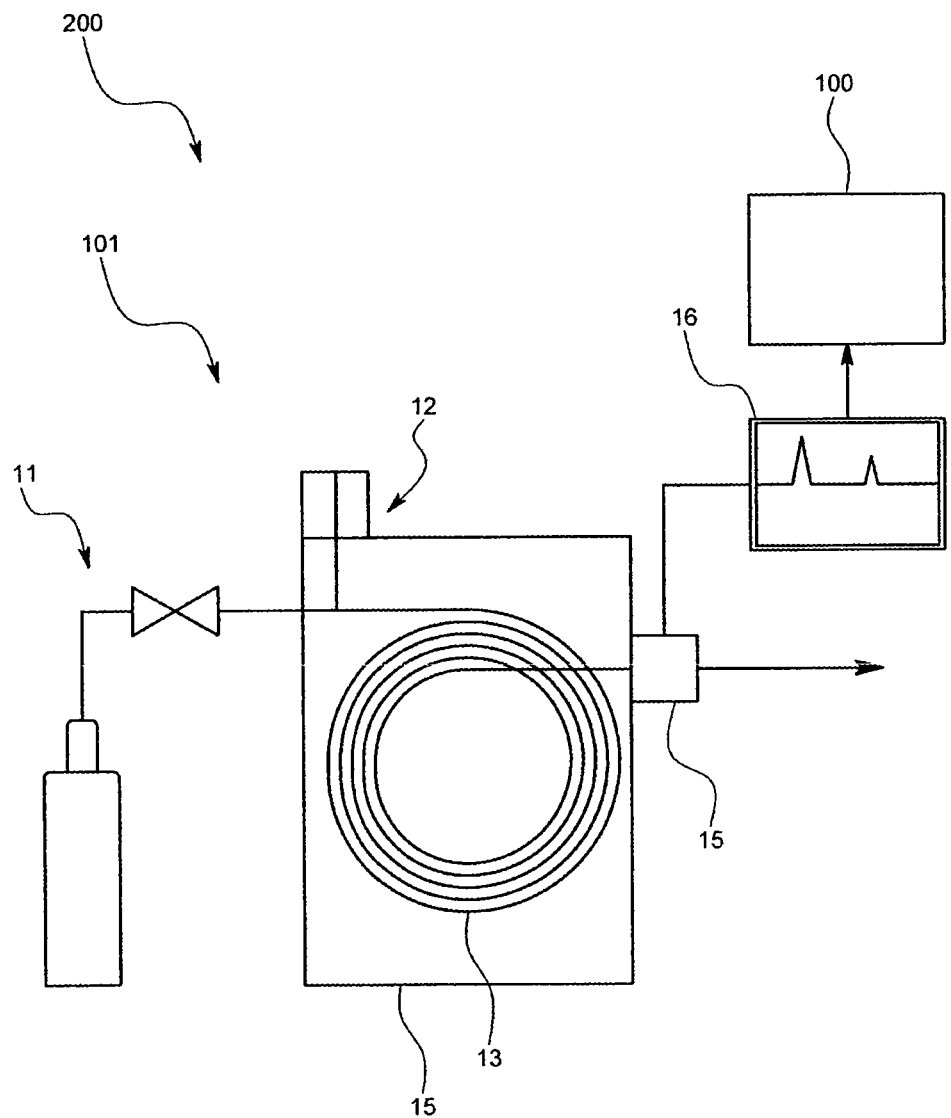
FIG. 1 is a schematic diagram illustrating the whole of an analysis system according to a first embodiment of the present invention.

100 Data processing device for gas chromatograph
4 Receiving part
6 Known RI data storage part
7 Known RI data conversion part
71 Known temperature RT conversion part
72 Isothermal analysis temperature RT calculation part
73 RI calculation part
74 RI temperature function storage part
75 Temperature substitution operating part
76 Distribution coefficient function identifying part
77 Temperature rising condition RT calculation part
78 Temperature rising condition RI calculation part
8 Post-conversion RI data storage part
9 Search part

DESCRIPTION OF EMBODIMENTS

A first embodiment of the present invention is described referring to the drawings.

A data processing device for a gas chromatograph 100 in the first embodiment is one that is used to, from only a retention index of an unknown sample X, which was obtained by gas chromatographic analysis, identify which registered substance $G_n$ the unknown sample X is. That is, as illustrated in FIG. 1, the data processing device for a gas chromatograph 100 constitutes an analysis system 200 in combination with a gas chromatograph 101.

The gas chromatograph 101 is one that is provided with: a column 13 that is a tube coated with a stationary phase inside; a carrier gas introduction part 11 for introducing carrier gas, which is used as a mobile phase, into the column 13; a sample introduction part 12 for introducing a sample desired to be qualified, such as an unknown sample X, into the column 13; a column oven 14 for keeping temperature of the column 13 constant or raising the temperature at a constant rate; a sensing part 15 that, on an outlet side of the column, senses a passing substance to output an electrical signal; and a retention time measuring part 16 that, on the basis of the electrical signal outputted from the sensing part 15, measures a retention time that is a time required for each sample to reach an outlet of the column 13 from the introduction of the sample.

In the present embodiment, the data processing device for a gas chromatograph 100 is adapted to, on the basis of a retention time or an adjusted retention time of the unknown sample, which is outputted from the retention time measuring part 15, identify and output which of registered substances $G_n$ already registered in a library the unknown sample X corresponds to.

Figure 2:
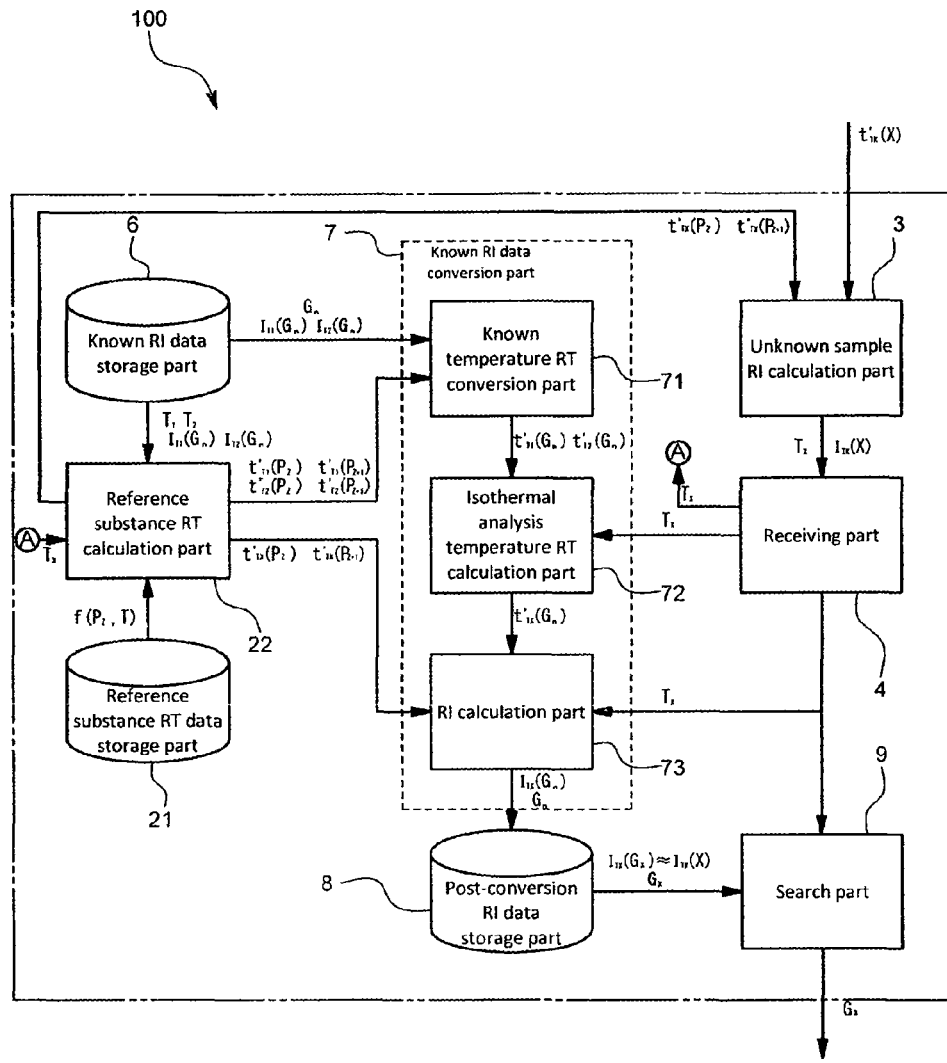
FIG. 2 is a functional block diagram illustrating a data processing device for a gas chromatograph in the first embodiment.

The data processing device for a gas chromatograph 100 is a so-called computer provided with a memory, a CPU, an A/D converter, an input/output interface, a monitor, and the like, and configured to, in such a manner that the CPU executes a data processing program for a gas chromatograph stored in the memory, fulfill various types of functions to output which of the registered substances $G_n$ the unknown sample X corresponds to on the basis of an inputted retention index of the unknown sample X. That is, the data processing device for a gas chromatograph 100 is, as illustrated in FIG. 2, configured to fulfill functions as, at least, a reference substance RT data storage part 21, a reference substance RT calculation part 22, an unknown sample RI calculation part 73, a receiving part 4, a known RI data storage part 6, a known RI data conversion part 7, a post-conversion RI data storage part 8, and a search part 9.

The respective parts are sequentially described. Note that, in the following description, the gas chromatographic analysis in the first embodiment is performed as isothermal analysis, and an isothermal analysis temperature $T_x$ that is a temperature at the time of measuring the adjusted retention time of the unknown sample X is used to provide the description.

The reference substance RT data storage part 21 is one that stores a function for, from a temperature, calculating an adjusted retention time of a reference substance P, which is used to actually measure a retention index. More specifically, the reference substance P is an alkane, and there is a proportional relationship between a logarithm of an adjusted retention time of the alkane and a reciprocal of an absolute temperature, so that the reference substance RT data storage part 21 stores a relational expression like Expression 2.

$$\log t'_T(P_Z) = a(P_Z) * (1/T) + b(P_Z) \quad \text{[Expression 2]}$$

Here, $t_T'(P_Z)$: an adjusted retention time of an alkane having a carbon number of Z at a temperature T, T: an absolute temperature, and $a(P_Z)$ and $b(P_Z)$: constants that are specific to each alkane carbon number. Note that the respective constants are experimentally obtained in advance for all alkanes used in the present embodiment. In addition, if the constants of some alkane are unknown, the respective constants can also be calculated from alkanes respectively having different carbon numbers.

Figure 3:
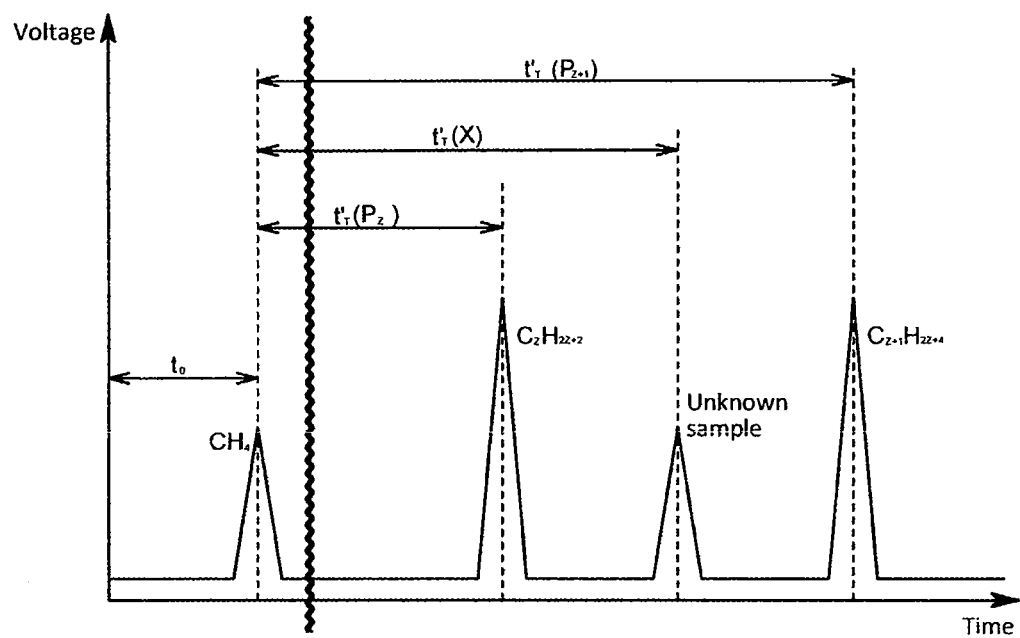
FIG. 3 is a schematic graph illustrating a concept of a retention time and an adjusted retention time.

Also, the adjusted retention time has a value obtained by, as illustrated in FIG. 3, from a retention time measured by the gas chromatograph 101, subtracting a retention time of a constituent not retained in the column 13, such as $CH_4$.

The reference substance RT calculation part 22 is one that calculates an adjusted retention time of the reference substance P at a required temperature on the basis of the above-described expression. In the present embodiment, the reference substance RT calculation part 22 is configured to be inputted with a temperature at the time of actually measuring a retention index of an after-mentioned registered substance $G_n$ or a temperature at the time of measuring the retention index of the unknown sample X, and output a value required for operations in respective parts.

The unknown sample RI calculation part 73 is one that, on the basis of the adjusted retention time of the unknown sample, which was measured by the gas chromatograph 101, and an adjusted retention time of the reference substance P under a temperature condition at the time of the measurement, calculates the retention index of the actually measured unknown sample X. More specifically, the unknown sample RI calculation part 73 is adapted to input the isothermal analysis temperature $T_X$ at which the adjusted retention time of the unknown sample X was measured to the reference substance RT calculation part 22, and obtain an adjusted retention time of the reference substance P at the temperature. Also, the unknown sample RI calculation part 73 is one that, on the basis of a retention index definition given by Expression 3, calculates the retention index of the actually measured unknown sample X, and adapted to input a value of the retention index to the receiving part 4.

$$I_{TX}(X) = \frac{\log t'_{TX}(X) - \log t'_{TX}(P_z)}{\log t'_{TX}(P_{z+1}) - \log t'_{TX}(P_z)} \times 100 + 100 \times Z \quad \text{[Expression 3]}$$

Here, $I_{TX}(X)$: the retention index of the unknown sample X at the isothermal analysis temperature $T_X$, $t'_{TX}(X)$: the adjusted retention time of the unknown sample X at the isothermal analysis temperature $T_X$, $t'_{TX}(P_Z)$: an adjusted retention time of an alkane having a carbon number of Z at the isothermal analysis temperature $T_X$, $t'_{TX}(P_{Z+1})$: an adjusted retention time of an alkane having a carbon number of Z+1 at the isothermal analysis temperature $T_X$, and Z: a carbon number.

The receiving part 4 is one that receives a predetermined temperature condition at the time of actually measuring the retention index on the unknown sample X, and a value related to the retention index actually measured on the unknown sample X by gas chromatographic analysis using the predetermined temperature condition. In the present embodiment, the predetermined temperature condition refers to the isothermal analysis temperature $T_X$ at the time of isothermally analyzing the unknown sample X by the gas chromatograph 101, and the present embodiment is adapted to, regarding the retention index of the unknown sample X, receive the value calculated in the unknown sample RI calculation part 73. Regarding the retention index, the receiving part 4 may be adapted to receive, for example, the adjusted retention time or the like that is the related value. Also, although not explicitly illustrated in FIG. 2, the receiving part 4 also receives the type of the stationary phase used when the gas chromatographic analysis of the unknown sample was performed, and the after-mentioned search part 9 is adapted to qualify the unknown sample X with use of data on the registered substance $G_n$ measured with use of the same stationary phase.

The known RI data storage part 6 is a library that records a number of chemical substance-based retention indices collected by, for example, NIST or the like, and one that stores a plurality of pieces of known RI data each in which an identifier specific to each of the registered substances $G_n$, and retention indices of a registered substance $G_n$ indicated by the identifier, which were actually measured by gas chromatographic analysis at a plurality of different temperatures, are paired. In other words, the known RI data storage part 6 stores, together with a chemical formula or a name of the registered substance $G_n$ as the identifier as listed in a table of FIG. 4, retention indices together with measurement temperatures as a pair. Note that in some cases, the known RI data storage part 6 stores only one retention index at one measurement temperature for one registered substance $G_n$; however, such a registered substance $G_n$ is not used for retention index conversion.

The known RI data conversion part 7 is configured to convert a retention index in known RI data stored in the known RI data storage part 6 to a retention index at the isothermal analysis temperature $T_X$ received by the receiving part 4. More specifically, the known RI data conversion part 7 is configured to include: a known temperature RT conversion part 71 that, from a retention index of a registered substance $G_n$ stored in the known RI data storage part 6, calculates an adjusted retention time at a known temperature at the time of measuring the retention index; an isothermal analysis temperature RT calculation part 72 that, from the adjusted retention time at the known temperature, which was calculated in the known temperature RT conversion part 71, calculates an adjusted retention time at the time of the isothermal analysis; and an RI calculation part 73 that, from the adjusted retention time at the time of the isothermal analysis, calculates a retention index at the isothermal analysis temperature $T_X$.

The known temperature RT conversion part 71 is configured to, from the known RI data storage part 6, obtain retention indices at a first temperature $T_1$ and a second temperature $T_2$, which are two different temperatures, for a registered substance $G_n$ indicated by one identifier, as well as, from the reference substance RT calculation part 22, obtaining adjusted retention times of two reference substances P at the first temperature $T_1$ and adjusted retention times of the two reference substances P at the second temperature $T_2$. Also, the known temperature RT conversion part 71 is configured to, on the basis of the obtained values, from Expression 4, calculate an adjusted retention time of the registered substance $G_n$ at the isothermal analysis temperature $T_x$. Note that the first temperature $T_1$ and the second temperature $T_2$ may respectively take different values for each of the registered substances $G_n$.

$$\log t'_{T1}(G_n) = \log t'_{T1}(P_z) + (I_{T1}(G_n) - 100 \times Z)(\log t'_{T1}(P_{z+1}) - \log t'_{T1}(P_z))/100$$

$$\log t'_{T2}(G_n) = \log t'_{T2}(P_z) + (I_{T2}(G_n) - 100 \times Z)(\log t'_{T2}(P_{z+1}) - \log t'_{T2}(P_z))/100 \quad \text{[Expression 4]}$$

Here, $I_{T1}(G_n)$ and $I_{T2}(G_n)$: the retention indices of the registered substance $G_n$ at the known temperatures $T_1$ and $T_2$; $t'_{T1}(G_n)$ and $t'_{T2}(G_n)$: the adjusted retention times of the registered substance $G_n$ at the known temperatures $T_1$ and $T_2$; $t'_{T1}(P_Z)$ and $t'_{T2}(P_Z)$: the adjusted retention times of an alkane having a carbon number of Z at the known temperatures $T_1$ and $T_2$; $t'_{T1}(P_{Z+1})$ and $t'_{T2}(P_{Z+1})$: the adjusted retention times of an alkane having a carbon number of Z+1 at the known temperatures $T_1$ and $T_2$; and Z: a carbon number. In addition, in the case of using a Gauss symbol [ ] to represent the carbon number Z, Z is an integer selected by $Z=[I_{T1}(G_n)]$ in the case of the upper expression of Expression 4, or $Z=[I_{T2}(G_n)]$ in the case of the lower expression of Expression 4.

From Expression 4, the adjusted retention times of the registered substance $G_n$ at the known temperatures are calculated. Regarding the adjusted retention times $t'_{T1}(G_n)$ and $t'_{T2}(G_n)$ of the registered substance $G_n$ at the known temperatures $T_1$ and $T_2$, experimental conditions other than the temperatures, such as a linear velocity, are ones that correspond to values measured at a linear velocity at the time of measuring the adjusted retention times of the alkanes at the known temperatures $T_1$ and $T_2$.

The isothermal analysis temperature RT calculation part 72 is configured to, on the basis of a linear relationship between reciprocals of the first and second temperatures $T_1$ and $T_2$ and logarithms of the adjusted retention times of the registered substance $G_n$ corresponding to the temperatures, calculate an adjusted retention time of the registered substance $G_n$ at the isothermal analysis temperature $T_X$. That is, the isothermal analysis temperature RT calculation part 72 is one that calculates the adjusted retention time of the registered substance $G_n$ at the isothermal analysis temperature $T_X$ from Expression 5.

$$\log t'_{TX}(G_n) = \frac{\log t'_{T2}(G_n) - \log t'_{T1}(G_n)}{1/T_2 - 1/T_1}\left(\frac{1}{T_x}\right) + \frac{(1/T_2)\log t'_{T1}(G_n) - 1/T_1\log t'_{T2}(G_n)}{1/T_2 - 1/T_1} \quad \text{[Expression 5]}$$

Here, $T_X$: the isothermal analysis temperature, and $t'_{Tx}(G_n)$: the adjusted retention time of the registered substance $G_n$ at the isothermal analysis temperature $T_X$. As described above, the experimental conditions for $t'_{T1}(G_n)$ and $t'_{T2}(G_n)$, such as the linear velocity, correspond to those at the time of measuring the adjusted retention times of the alkanes, and therefore $t'_{Tx}(G_n)$ is also converted to one at the time of measuring the adjusted retention times of the alkanes. Accordingly, such adjusted retention times may be different in experimental conditions such as a linear velocity from the adjusted retention time measured on the unknown sample, and therefore values thereof cannot be directly used for comparison.

The RI calculation part 73 is one that, on the basis of the adjusted retention time of the registered substance $G_n$ at the isothermal analysis temperature $T_X$, which is calculated in the isothermal analysis temperature RT calculation part 72, and the adjusted retention times of the reference substances P at the isothermal analysis temperature $T_X$, which are calculated in the reference substance RT calculation part 22, calculates the retention index of the registered substance $G_n$ at the isothermal analysis temperature $T_X$ from Expression 6, and outputs a value of the retention index and the identifier to the post-conversion RI data storage part 8 as a pair.

$$I_{TX}(G_n) = \frac{\log t'_{TX}(G_n) - \log t'_{TX}(P_z)}{\log t'_{TX}(P_{z+1}) - \log t'_{TX}(P_z)} \times 100 + 100 \times Z \quad \text{[Expression 6]}$$

Here, $I_{TX}(G_n)$: the retention index of the registered substance $G_n$ at the isothermal analysis temperature $T_X$, and as Z: a carbon number, the carbon number meeting a relationship of $t'_{TX}(P_z) < t'_{TX}(G_n) < t'_{TX}(P_{z+1})$ is selected.

As illustrated in FIG. 5, the post-conversion RI data storage part 8 stores pieces of post-conversion RI data each in which a retention index of a registered substance $G_n$ under the predetermined temperature condition, which were converted by the known RI data conversion part 7, and a corresponding identifier are paired. Differently from the known RI data storage part 6, the post-conversion RI data storage part 8 stores one retention index at the isothermal analysis temperature $T_X$ for one registered substance $G_n$.

The search part 9 is one that extracts, from among the pieces of post-conversion RI data stored in the post-conversion RI data storage part 8, data including a retention index coincident with or substantially equal to a value of the retention index of the unknown sample X under the predetermined temperature condition, which was received in the receiving part 4, and outputs an identifier corresponding to the extracted retention index.

Figure 6:
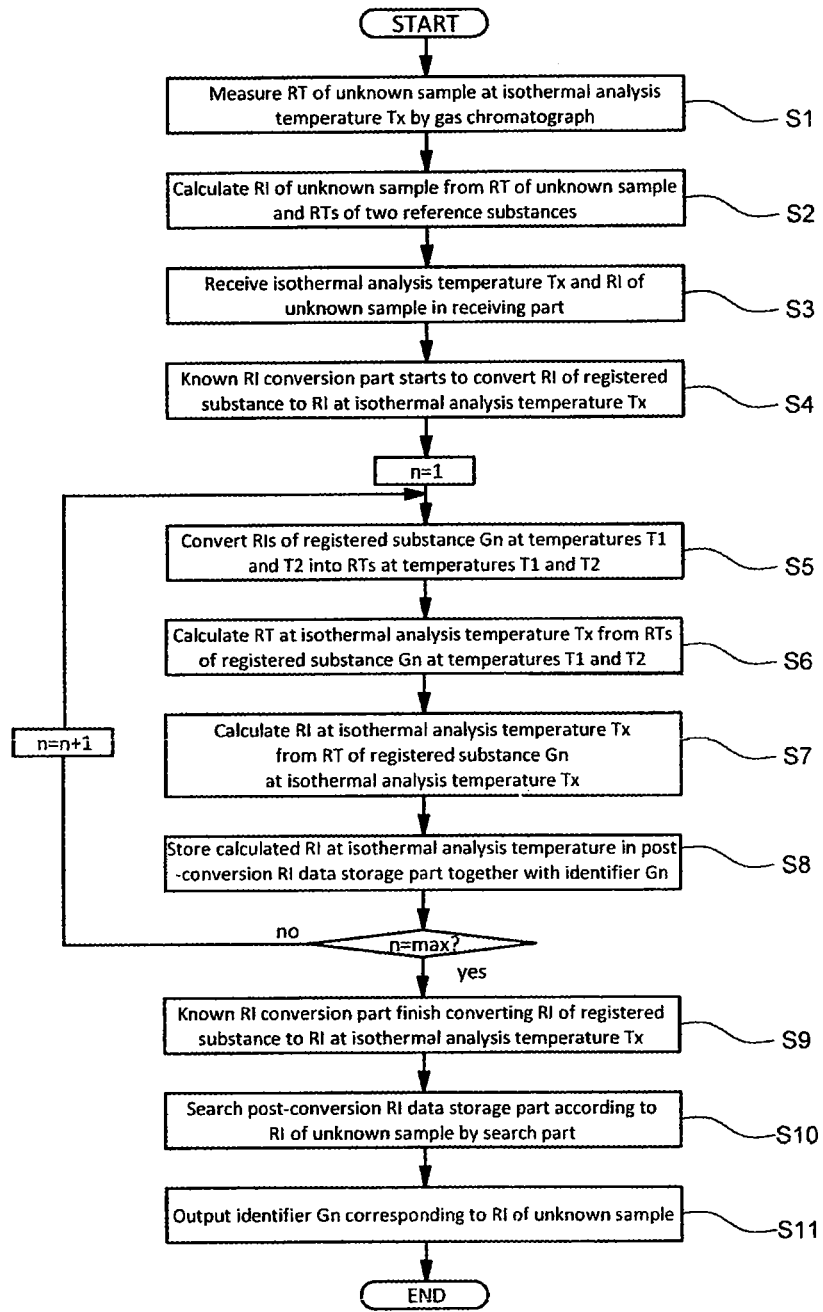
FIG. 6 is a flowchart illustrating operation of the data processing device for a gas chromatograph in the first embodiment.

Operation of the data processing device for a gas chromatograph 100 configured as described is described on the basis of a flowchart in FIG. 6.

First, an adjusted retention time of an unknown sample X is measured at a measured isothermal analysis temperature $T_X$ by the gas chromatograph 101 (Step S1). The unknown sample RI calculation part 73 calculates a retention index of the unknown sample X from the measured adjusted retention time of the unknown sample X and adjusted retention times of reference substances P, which were calculated by the reference substance RT calculation part 22 (Step S2).

After that, in the receiving part 4, the isothermal analysis temperature $T_X$ used for the measurement, and the calculated retention index of the unknown sample X are received (Step S3), on the basis of which the known RI data conversion part 7 starts to convert from known retention indices of registered substances $G_n$ to retention indices at the isothermal analysis temperature $T_X$ (Step S4).

First, regarding a registered substance $G_n$ that is stored in the known RI data storage part 6 and has an identifier of G1, the known temperature RT conversion part 71 converts from the adjusted retention times of the reference substances P and retention indices, which were measured in the past at a first temperature $T_1$ and a second temperature $T_2$, to adjusted retention times of the registered substance $G_n$ at the first temperature $T_1$ and the second temperature $T_2$ (Step S5).

Then, in the isothermal analysis temperature RT calculation part 72, from the adjusted retention times of the registered substance $G_n$ at the first temperature $T_1$ and the second temperature $T_2$, an adjusted retention time of the registered substance $G_n$ at the isothermal analysis temperature $T_X$ is calculated by an operation using linearity (Step S6).

Finally, from the adjusted retention time of the registered substance $G_n$ at the isothermal analysis temperature $T_X$ and the adjusted retention times of the reference substances P, the RI calculation part 73 calculates a retention index of the registered substance $G_n$ at the isothermal temperature $T_X$ (Step S7), and the converted retention index is stored in the post-conversion RI data storage part 8 together with the identifier G1 (Step S8). The retention index converting operation steps S5 to S8 are performed until n reaches a maximum value to, for all of the registered substances stored in the known RI data storage part 6, convert to retention indices at the isothermal analysis temperature $T_X$, and thereby a new search set is prepared (Step S9).

Subsequently, the search part 9 searches the post-conversion RI data storage part 8 by the retention index of the unknown sample X (Step S10), and an identifier $G_n$ stored together with a close or coincident value among the converted retention indices is outputted (Step S11).

In this manner, what the unknown sample X is can be identified only by the gas chromatograph 101. That is, using the present inventors' findings that if there are retention indices at a plurality of different temperatures, it is possible to convert to a retention index under a predetermined temperature condition that is a condition other than temperature conditions under which the retention indices were measured, the present embodiment enables an unknown sample X to be identified only by gas chromatographic analysis.

Next, a second embodiment is described. Note that in the second embodiment, too, members in common with the first embodiment are provided with the same symbols, respectively.

In a data processing device for a gas chromatograph 100 in the second embodiment, a configuration and an operation of the known RI data conversion part 7 are different.

Figure 7:
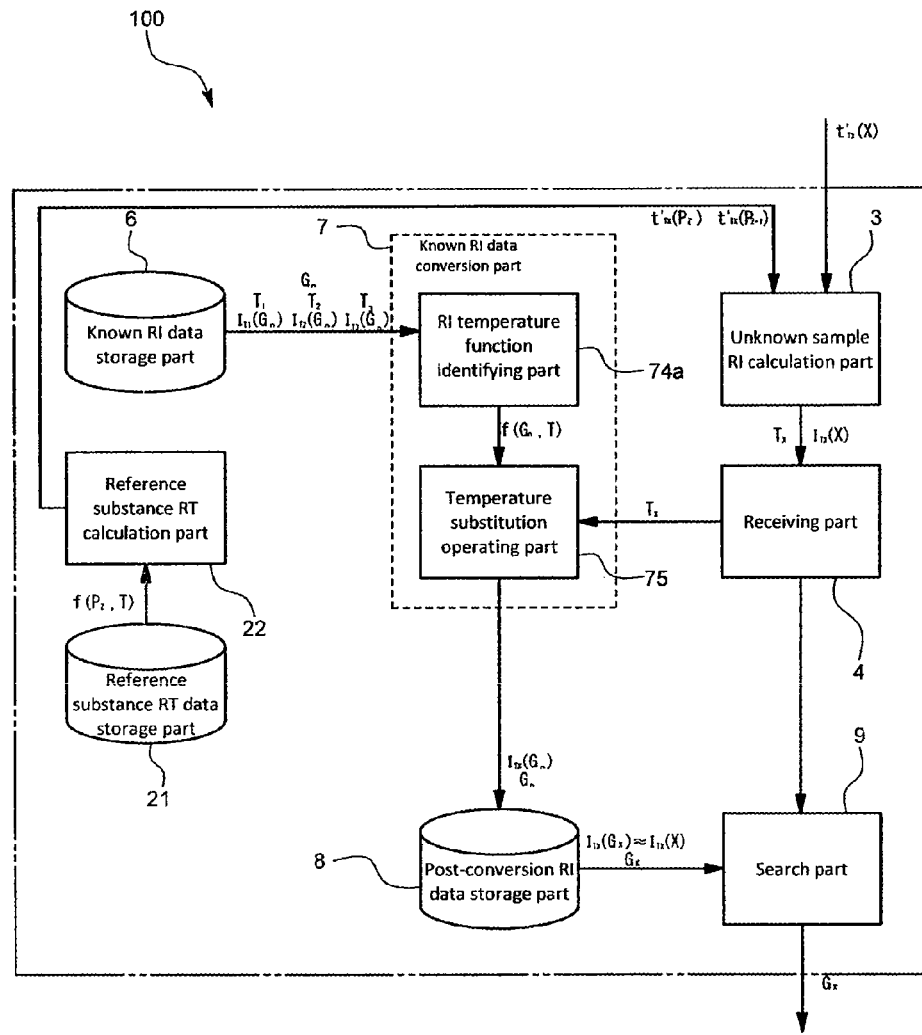
FIG. 7 is a functional block diagram illustrating a data processing device for a gas chromatograph in a second embodiment.

More specifically, as illustrated in FIG. 7, the known RI data conversion part 7 is characterized by being provided with: an RI temperature function identifying part 74 that, on the basis of retention indices of a registered substance $G_n$ at a first temperature $T_1$, second temperature $T_2$, and third temperature $T_3$ that are three different temperatures, identifies three constants of a conversion expression that is given by Expression 7 and a function of temperature; and a temperature substitution operating part 75 that substitutes an isothermal analysis temperature $T_X$ into the conversion expression identified by the RI temperature function identifying part 74, and thereby calculate a retention index of the registered substance $G_n$ at the isothermal analysis temperature $T_X$.

$$I = A + \frac{B}{T} + C \ln T \quad \text{[Expression 7]}$$

Here, I: the retention index; T: temperature; and A, B, and C: the constants identified from measured values of retention indices of each registered substance $G_n$.

To describe more specifically, the RI temperature function identifying part 74 is adapted to, from three temperatures and retention indices at the temperatures obtained from the known RI data storage part 6, identify the constants A, B, and C by, for example, a least squares method, and prepare the conversion expression for each registered substance $G_n$.

The temperature substitution operating part 75 is configured to obtain the conversion expression identified by the RI temperature function identifying part 74a and the isothermal analysis temperature $T_X$ received by the receiving part 4; calculate a retention index at the isothermal analysis temperature $T_X$ by substitution; and also store retention indices and identifiers of all registered substance $G_n$ in a post-conversion RI data storage part 8 as pairs.

Even such a known RI conversion part can convert to retention indices at various temperatures if there are retention indices at three different temperatures for each of the registered substances $G_n$. That is, as with the first embodiment, which of the registered substances $G_n$ an unknown sample X corresponds to can be identified only by a retention index of the unknown sample X.

Figure 8:
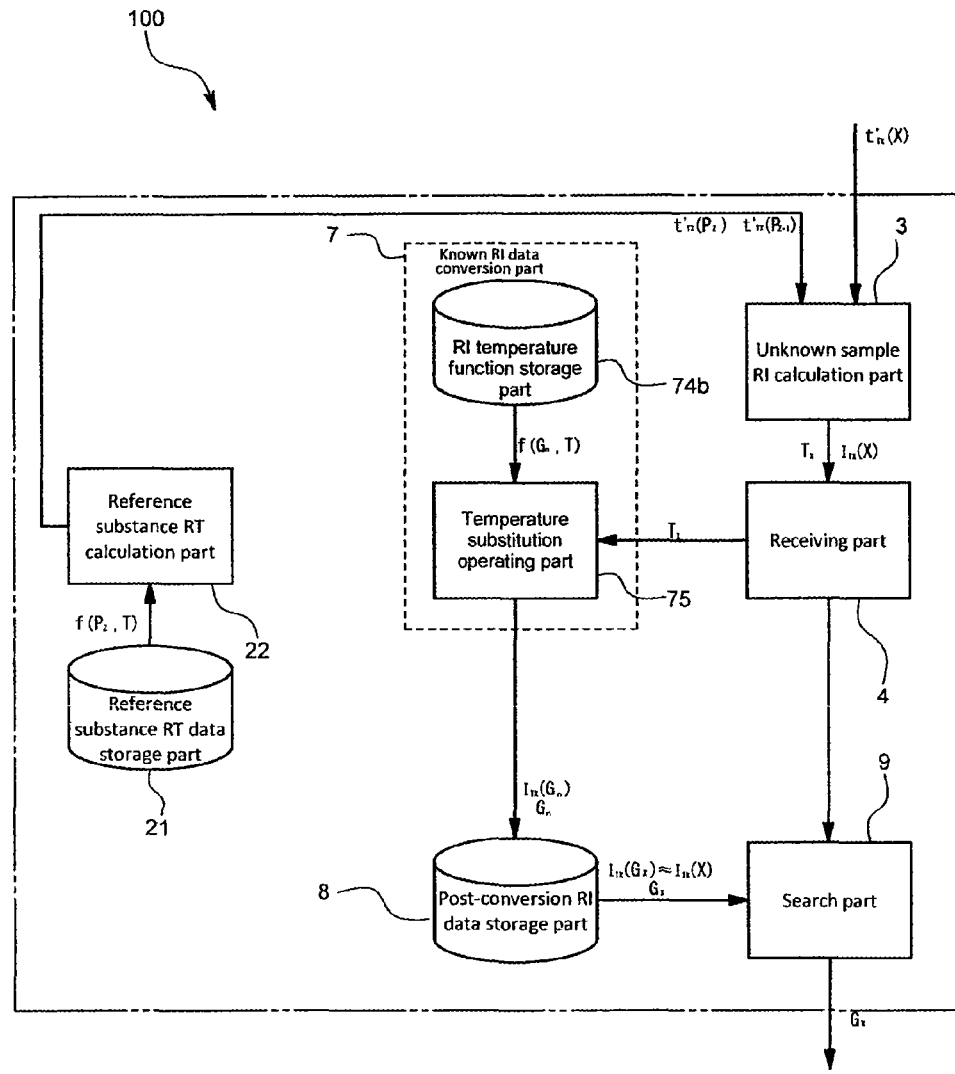
FIG. 8 is a functional block diagram illustrating a variation of the data processing device for a gas chromatograph in the second embodiment.

A variation of the second embodiment is described. The RI temperature function identifying part 74a prepares the conversion expression every time the receiving part 4 receives the retention index of the unknown sample X; however, as illustrated in FIG. 8, the present invention may be adapted to, for example, preliminarily prepare a conversion expression on the basis of a retention index of a registered substance $G_n$, which is registered in a library in advance, and a corresponding measurement temperature, and store the conversion expression for each registered substance $G_n$. That is, the RI temperature function identifying part 74a may be configured as an RI temperature function storage part 74b.

Next, a third embodiment is described. Note that in the third embodiment, too, members in common with the first embodiment are provided with the same symbols, respectively.

In the first and second embodiments, an unknown sample X is identified on the basis of an adjusted retention time at the time of performing the gas chromatographic analysis as the isothermal analysis; however, in the third embodiment, an unknown sample X is identified on the basis of an adjusted retention time obtained by temperature rising analysis.

Figure 9:
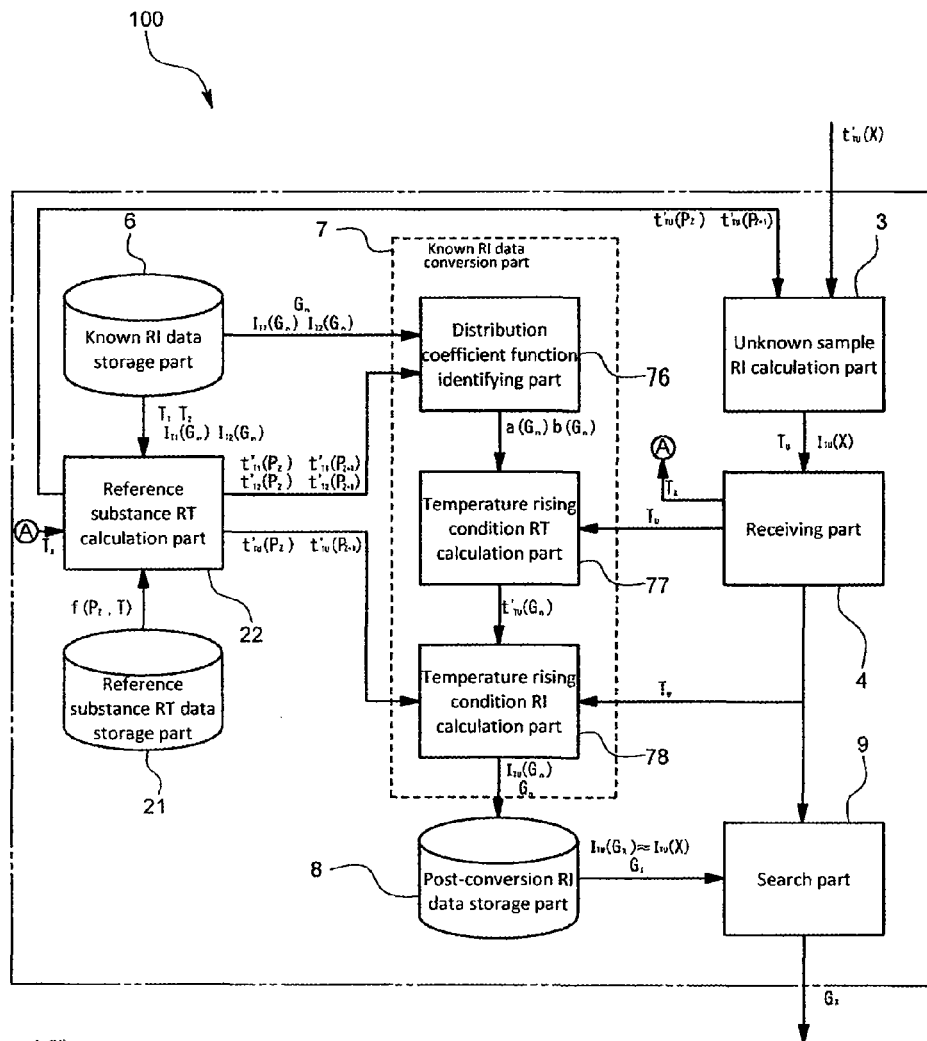
FIG. 9 is a functional block diagram illustrating a data processing device for a gas chromatograph in a third embodiment.

More specifically, a predetermined temperature condition includes a temperature rising condition $T_U$ adapted to include: a temperature rising rate that is appropriately set when gas chromatographic analysis is performed as the temperature rising analysis; and an initial setting temperature, and the known RI data conversion part 7 is, as illustrated in FIG. 9, one that is provided with: a distribution coefficient function identifying part 76 that, on the basis of retention indices of a registered substance $G_n$ at a first temperature $T_1$ and a second temperature $T_2$ that are two different temperatures, identifies a distribution coefficient of the registered substance $G_n$ as a function of temperature; a temperature rising condition RT calculation part 77 that, on the basis of the distribution coefficient and a length of a column 13 of a gas chromatograph 101, calculates an adjusted retention time of the registered substance $G_n$ under the temperature rising condition $T_U$; and a temperature rising condition RI calculation part 78 that, on the basis of the adjusted retention time of the registered substance $G_n$ under the temperature rising condition $T_U$, and adjusted retention times of reference substances P under the temperature rising condition $T_U$, calculates a retention index of the registered substance $G_n$ under the temperature rising condition $T_U$. Further, a reference substance RT calculation part 22 is also configured to have different operation at the time of the temperature rising analysis.

A reference substance RT calculation part 22 is configured to, from the temperature rising rate and the initial setting temperature of the temperature rising condition $T_U$ inputted to the receiving part 4, calculate an adjusted retention time of a reference substance P at the time of temperature rising. More specifically, the adjusted retention time is obtained by using the fact that between the adjusted retention time and temperature, there is a relationship as given by Expression 8.

$$t_{TU}(P_z) = t_0 \left(1 + \frac{K(P_z)}{\beta}\right) \quad \text{[Expression 8]}$$

$$\ln(K(P_z)) = a(P_z) \times \left(\frac{1}{T}\right) + b(P_z)$$

Here, $t_{TU}(P_Z)$: a retention time of an alkane having a carbon number of X under an isothermal condition; $K(P_Z)$: a distribution coefficient of the alkane having the carbon number Z; $a(P_Z)$ and $b(P_Z)$: constants that determine characteristics of the distribution coefficient; and T: absolute temperature.

From the above two expressions, the retention time $t_{TU}(P_Z)$ of the alkane having the carbon number of Z can be described as a function of temperature as given by Expression 9.

$$t_{TU}(P_z) = t_0 \left(1 + \exp\left(\frac{c(P_z)}{T} + d(P_z)\right)\right) \quad \text{[Expression 9]}$$

Here, $c(P_Z)$ and $d(P_Z)$ are constants based on the $a(P_Z)$ and $b(P_Z)$.

Further, given that the length of the column 13 is L, $L/t_T(P_Z)$ is a velocity at which the alkane travels inside the column 13 at some temperature, which becomes equal to the column 13 length L by being integrated with respect to the retention time $t_{TU}(P_Z)$ that is a time necessary for the alkane to reach an outlet of the column 13 from the start of elution in the gas chromatograph 101 under the temperature rising condition $T_U$, and therefore Expression 10 below holds.

$$L = \int_0^{t_U(P_z)} \frac{L}{t_0\left(1 + \exp\left(\frac{c(P_z)}{T} + d(P_z)\right)\right)} dt \quad \text{[Expression 10]}$$

Further, given that the temperature rising rate and the initial temperature of the temperature rising condition $T_U$ is r and Ti, respectively, variable conversion can be performed as T=r*t+Ti, and therefore Expression 10 is converted to Expression 11.

$$L = \int_0^{t_U(P_z)} \frac{L}{t_0\left(1 + \exp\left(\frac{c(P_z)}{r \times t + T_i} + d(P_z)\right)\right)} dt \quad \text{[Expression 11]}$$

The reference substance RT calculation part 22 is adapted to, on the basis of Expression 11, calculate the retention time $t_{TU}(P_z)$, and by subtracting the retention time under the temperature rising condition $T_U$ for $CH_4$ or the like, output the adjusted retention time under the temperature rising condition $T_U$. The adjusted retention time of the alkane under the temperature rising condition $T_U$ is used in an unknown sample RI calculation part 73 and the temperature rising condition RI calculation part 78.

The distribution coefficient function identifying part 76 is one that, from a retention index of a registered substance $G_n$ under the isothermal condition, which is stored in an RI data storage part 6, identifies a distribution coefficient. That is, the distribution coefficient function identifying part 76 is adapted to apply the expression given by above Expression 8 to each registered substance $G_n$ to convert to Expression 12, and also identify a distribution coefficient from Expression 13 resulting from performing expression conversion so as to meet a registered retention index under the isothermal condition. Specifically, Expressions 12 and 13 are as follows.

$$t_T(G_n) = t_0\left(1 + \frac{K(G_n)}{\beta}\right) \Rightarrow K(G_n) = \quad \text{[Expression 12]}$$
$$(t_T(G_n) - t_0)\frac{\beta}{t_0} \Rightarrow K(G_n) = t_T'(G_n)\frac{\beta}{T_0}$$
$$\ln(K(G_n)) = a(G_n) \times \left(\frac{1}{T}\right) + b(G_n)$$

Here, $t'_T(G_n)$: an adjusted retention time of the registered substance $G_n$ at a temperature T under the isothermal condition, which as described in the first embodiment, too, has a value calculable from a retention index at the temperature T under the isothermal condition, and therefore from Expression 12 and two expressions at temperatures $T_1$ and $T_2$ of Expression 13, $a(G_n)$ and $b(G_n)$ can be identified.

$$\ln\left(t'_{T1}(G_n)\frac{\beta}{t_0}\right) = a(G_n) \times \left(\frac{1}{T_1}\right) + b(G_n) \quad \text{[Expression 13]}$$
$$\ln\left(t'_{T2}(G_n)\frac{\beta}{t_0}\right) = a(G_n) \times \left(\frac{1}{T_2}\right) + b(G_n)$$

The temperature rising condition RT calculation part 77, is, as with the reference substance RT calculation part 22, adapted to, on the basis of the column 13 length L, and a time function of a retention time of the registered substance $G_n$ under the isothermal condition, calculate a retention time of the registered substance $G_n$ under the temperature rising condition $T_U$ from Expression 14. Further, the temperature rising condition RT calculation part 77 is adapted to, from the calculated retention time, output an adjusted retention time to the temperature rising condition RI calculation part 78.

$$L = \int_0^{t_U(G_n)} \frac{L}{t_0\left(1 + \exp\left(\frac{c(G_n)}{r \times t + T_i} + d(G_n)\right)\right)} dt \quad \text{[Expression 14]}$$

Here, $c(G_n)$ and $d(G_n)$: constants based on $a(G_n)$ and $b(G_n)$, and $t_{TU}(G_n)$: the retention time of the registered substance $G_n$ under the temperature rising condition $T_U$.

On the basis of the adjusted retention times of the reference substances P under the temperature rising condition $T_U$, which are outputted from the reference substance RT calculation part 22, and the adjusted retention time of the registered substance $G_n$ under the temperature rising condition $T_U$, which is outputted from the temperature rising condition RT calculation part 77, the temperature rising condition RI calculation part 78 calculates the retention index of the registered substance $G_n$ under the temperature rising condition $T_U$ from Expression 15.

$$I_{TU}(G_n) = \frac{t'_{TU}(G_n) - t'_{TU}(P_z)}{t'_{TU}(P_{z+1}) - t'_{TU}(P_z)} \times 100 + 100 \times Z \quad \text{[Expression 15]}$$

Then, in a post-conversion RI data storage part 8, the retention index of the registered substance $G_n$ under the temperature rising condition $T_U$ is stored together with a corresponding identifier. The search part 9 compares the retention index of the unknown sample X under the temperature rising condition $T_U$ and the retention index of the registered substance $G_n$ under the same temperature rising condition $T_U$, which is stored in the post-conversion RI storage part with each other to output which registered substance $G_n$ the unknown sample X corresponds to. Thus, even in the case where analysis in the gas chromatograph 101 is performed under the temperature rising condition $T_U$, the unknown sample X can be identified only by the analysis by the gas chromatograph 101.

Next, a fourth embodiment is described. Note that in the fourth embodiment, too, members in common with the first embodiment are provided with the same symbols, respectively.

Each of the above-described embodiment is configured such that, from among pieces of post-conversion RI data stored in the post-conversion RI data storage part 8, the search part 9 extracts data including a retention index coincident with or substantially equal to a retention index of an unknown sample X under the predetermined temperature condition, which was received by the receiving part 4, and output a corresponding registered substance $G_n$. On the other hand, the fourth embodiment is different from each of the above-described embodiments in being configured to, in the receiving part 4, receive a plurality of retention indices of an unknown sample X, which were measured under measurement conditions respectively including different analysis temperatures or different stationary phase types used for the measurement.

Further, in the fourth embodiment, a search part 9 is configured to, on the basis of a received retention index of the unknown sample X under each of the measurement conditions, extract, from a post-conversion RI data storage part 8, a candidate set including a plurality of candidate registered substances $G_n$ that may correspond to the unknown sample X. Also, the search part 9 is configured to finally output an identifier of a registered substance $G_n$ common to the respective candidate sets extracted on the basis of respective combinations each including each of the measurement conditions and a retention index of the unknown sample X, which was measured under the measurement condition.

Figure 10:
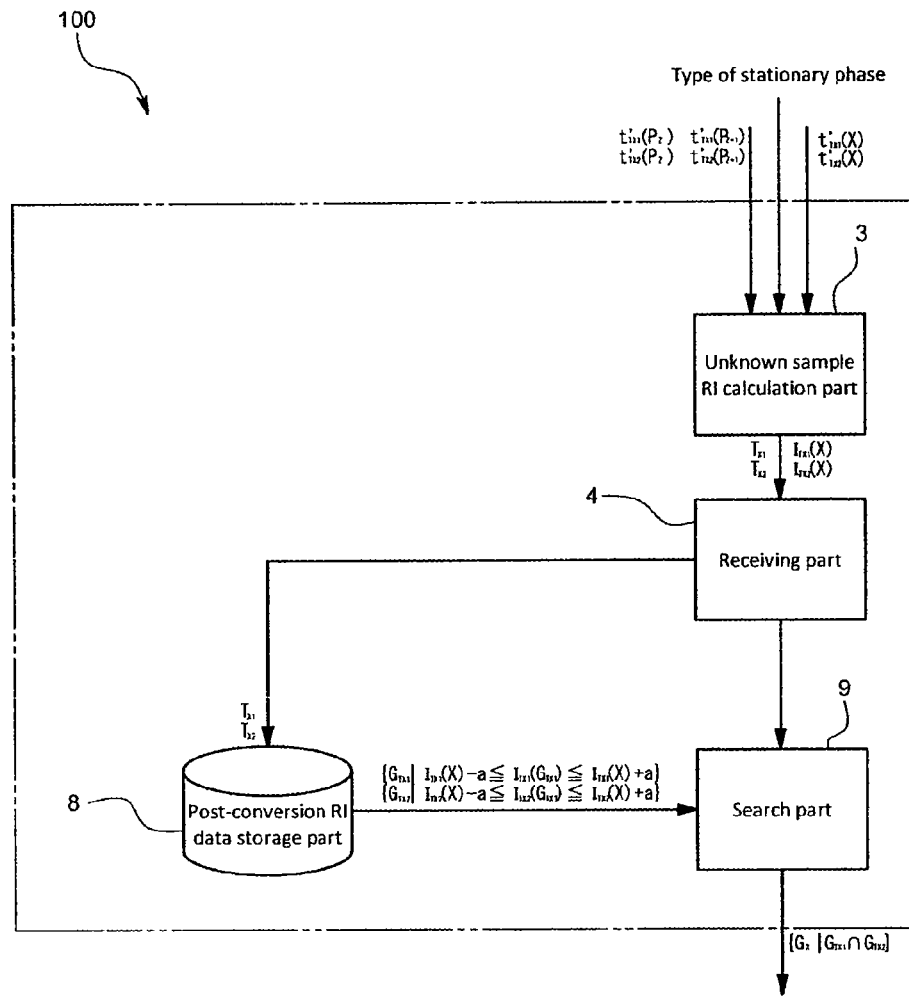
FIG. 10 is a functional block diagram illustrating a data processing device for a gas chromatograph in a fourth embodiment.

In the following, described is operation in the fourth embodiment by taking a specific example where two measurement results that were measured on some unknown sample X at different isothermal analysis temperatures $T_{X1}$ and $T_{X2}$ with use of the same stationary phase are received by the receiving part 9, and from retention indices $I_{TX1}(X)$ and $I_{TX2}(X)$ at the respective temperatures $T_{X1}$ and $T_{X2}$, the search part 9 prepares two candidate sets $G_{TX1}$ and $G_{TX2}$ of relevant registered substances $G_n$ to output a final candidate compound from the two candidate sets $G_{TX1}$ and $G_{TX2}$. In addition, a data processing device for a gas chromatograph 100 in the fourth embodiment converts a known retention index of a registered substance $G_n$ to retention indices $I_{TX1}(X)$ and $I_{TX2}(X)$ at the respective isothermal analysis temperatures $T_{X1}$ and $T_{X2}$ to form a database by the method as described in any of the above first to third embodiments, and then stores the database in the post-conversion RI data storage part 8 in advance. Also, as illustrated in FIG. 10, the search part 9 is configured to, from the database of the post-conversion RI data storage part 8, search for registered substances $G_n$ having retention indices $I_{TX1}(G_n)$ and $I_{TX2}(G_n)$ within ranges of a predetermined value a inclusive with respect to values of the retention indices $I_{TX1}(X)$ and $I_{TX2}(X)$ of the unknown sample X at the inputted analysis temperatures $T_{X1}$ and $T_{X2}$ at the time of gas chromatographic analysis of the unknown sample X, and obtain search results as the candidate sets $G_{TX1}$ and $G_{TX2}$, respectively.

First, assuming that at the first isothermal analysis temperature $T_{X1}$, an adjusted retention time $t'_{TX1}(X)$ of the unknown sample X is measured, an unknown sample RI calculation part 3 calculates the first retention index $I_{TX1}(X)$ of the unknown sample X from adjusted retention times $t'_{TX1}(P_Z)$ and $t'_{TX1}(P_{Z+1})$ of alkanes at the first isothermal analysis temperature $T_{X1}$. It is here assumed that the value of the first retention index $I_{TX1}(X)$ is, for example, 860.4.

When the receiving part 4 receives the first isothermal analysis temperature $T_{X1}$ and the first retention index $I_{TX1}(X)$ of the unknown sample X, the search part 9 searches the post-conversion RI data storage part 8 to extract registered substances $G_n$ having the retention indices $I_{TX1}(G_n)$ of which absolute values of differences from the first retention index $I_{TX1}(X)$ are equal to or less than the predetermined value a, and obtains the first candidate set $G_{TX1}$ including the plurality of relevant candidates. It is here assumed that as the first candidate set $G_{TX1}$, as illustrated in FIG. 11(a), for example, registered substances $G_n$ respectively having retention indices within a range of ±10 inclusive with respect to 860.4 that is the value of the first retention index $I_{TX1}(X)$ are extracted.

Then, assuming that at the second isothermal analysis temperature $T_{X2}$ that is a different temperature from the first isothermal analysis temperature $T_{X1}$, an adjusted retention time $t'_{TX2}(X)$ of the unknown sample X is measured, the unknown sample RI calculation part 3 calculates the second retention index $I_{TX2}(X)$ of the unknown sample X from adjusted retention times $t'_{TX2}(P_Z)$ and $t'_{TX2}(P_{Z+1})$ of the alkanes at the second isothermal analysis temperature $T_{X2}$. Note that depending on the value of the second retention index $I_{TX2}(X)$, the types of alkanes to be used for the calculation may be different from those at the time of calculating the first retention index $I_{TX1}(X)$. Also, it is here assumed that the value of the second retention index $I_{TX2}(X)$ is, for example, 852.8.

Subsequently, the receiving part 4 and the search part 9 perform similar operations to those described above, and thereby the second candidate set $G_{TX2}$ at the second isothermal analysis temperature $T_{X2}$ is obtained by the search part 9. As a result, it is assumed that the second candidate set $G_{TX2}$ as illustrated in FIG. 11(b) is extracted.

Finally, the search part 9 extracts a registered substance $G_n$ common to the first candidate set $G_{TX1}$ and the second candidate set $G_{TX2}$ to output it as a result $G_X$ of identifying the unknown sample X. That is, in FIGS. 11(a) and (b), the common element is only a registered substance $G_4$ indicated by hatched lines, and therefore the unknown sample X is qualified as the registered substance $G_4$, which is outputted from the search part 9.

As described, according to the data processing device for a gas chromatograph 100 in the fourth embodiment, on the basis of retention indices of an unknown sample X under a plurality of different measurement conditions, a plurality of relevant candidate registered substances $G_n$ can be narrowed down to make a quality determination. Accordingly, even in the case where due to the presence of a measurement error or the like caused by a chromatograph, retention indices are not coincident with each other, a corresponding substance can be identified, and qualifying accuracy of the substance can also be increased.

A variation of the fourth embodiment is also described.

In the fourth embodiment, as an example of the different measurement conditions, described is the case where the isothermal analysis temperatures are different; however, even in the case where an actually measured retention index results from measurement by temperature rising analysis as described in the third embodiment, a qualifying method in the fourth embodiment can be applied. That is, a plurality of retention indices respectively under different temperature rising analysis conditions may be used to qualify an unknown sample. Also, an unknown sample may be qualified on the basis of two retention indices actually measured under different temperature-related measurement conditions. The present invention may be adapted such that, for example, two retention indices, i.e., a retention index actually measured on an unknown sample at some isothermal analysis temperature, and a retention index actually measured at some temperature rising analysis temperature, are used to prepare candidate sets for the retention indices, and the search part outputs one common to the respective candidate sets.

Further, an unknown sample may be qualified by using the fact that retention indices measured in the case of different stationary phases respectively take different values. That is, as illustrated in FIG. 10, the receiving part and the search part may be configured to receive stationary phase types to qualify an unknown sample from retention indices of a registered substance, which were respectively measured with use of the same stationary phases as those used to measure the unknown sample, and the search part may be configured to use a plurality of retention indices of the unknown sample, which were measured with use of different stationary phases, to prepare candidate sets for the respective retention indices, and output a registered substance common to the respective candidate sets.

Specifically, an unknown sample may be qualified from a plurality of retention indices measured on the unknown sample in the case where temperature conditions are the same, but stationary phases are different, or from retention indices of the unknown sample, which were measured under the conditions that both of the temperature conditions and the stationary phases are different.

In short, it is only necessary that the present invention is adapted to be able to, in the case where measurement conditions are set such that actually measured retention indices of an unknown sample take different values, prepare candidate sets from the plurality of retention indices measured under the respective measurement conditions to perform narrowing down.

Other embodiments are described.

In each of the above-described embodiments, as an example of a reference substance, an alkane is taken to use the so-called Kovats retention index; however, another substance may be used as the reference substance. For example, linear alcohol having a different carbon number in which one hydrogen atom of an alkane is replaced by a hydroxyl group may be used as the reference substance. In each of the above-described embodiments, the known RI data conversion part successively converts a known retention index in each analysis; however, for example, the present invention may preliminarily convert retention indices at temperatures that are potentially used at the time of analysis by a gas chromatograph, and store the converted retention indices in the post-conversion RI data storage part. By doing so, without waiting a time required to convert retention indices, the search part can immediately search for a retention index to shorten a time required to identify an unknown sample. Also, in each of the above-described embodiments, retention indices of all registered substances are converted; however, the present invention may be adapted to convert only registered substances respectively having retention indices that are within a predetermined range with respect to a retention index of an unknown sample. That is, the present invention may be adapted to convert retention indices of only registered substance, which may correspond to the unknown sample, among the registered substances by condition settings.

Also, as methods for determining the range where retention indices of registered substance stored in the known RI data storage part are converted include a method that determines the conversion range from an adjusted retention time of a reference substance such as an alkane at the time of performing gas chromatographic analysis of an unknown sample. More specifically, at the time of measuring an adjusted retention time of an unknown sample, an adjusted retention time of a reference substance is also measured by the same chromatographic analysis, and in the case where between a first adjusted retention time obtained for an alkane having a carbon number of Z and a second adjusted retention time obtained for another alkane having a carbon number of Z+1, the adjusted retention time of the unknown sample is present, a value of a retention index of the unknown sample can be estimated to be present between Z×100 to (Z+1)×100 from the definitional expression of Expression 6. Accordingly, the present invention may be adapted to convert, among retention indices stored in the known RI data storage part, only retention indices having values between Z×100 and (Z+1)×100, or only retention indices adjacent to the range to retention indices under a predetermined temperature condition.

In addition, the present invention may be adapted not to use, among the retention indices stored in the known RI data storage part, retention indices having incorrect values or having values by unreliable measurement for the retention index conversion. Specifically, it is only necessary that the known temperature RT conversion part eliminates incorrect values by using the fact that there is a proportional relationship between a logarithm of an adjusted retention time calculated from a retention index of a registered substance and a temperature at the time of measuring the retention index. That is, it is only necessary that the present invention is adapted to prepare a proportional expression on the basis of logarithms of adjusted retention times at two different temperatures, which were converted from retention indices of some registered substance at the two different temperatures, and the two different temperatures; to determine that a retention index not leading to an adjusted retention time at still another temperature even in the case of substituting the temperature into the proportional expression has a value by incorrect measurement or has a unreliable value, and not to use the retention index for the retention index conversion afterward.

The receiving part may be adapted to further receive pieces of information on other measurement conditions such as the type of a column, the type of a stationary phase used, and polarity of it. For example, in the case of comparing retention indices with each other, it is desirable that the types of columns, or the types of stationary phases are coincident with each other. Even in the case where the both are not coincident, retention indices respectively measured with use of stationary phases of which polarities are similar to each other may be compared.

For this reason, it is only necessary that the RI conversion part is adapted to convert, among the retention indices stored in the known RI data storage part, retention indices of only registered substances each having data indicating that the type of a registered stationary phase and the type of a stationary phase received by the receiving part are similar to each other. More specifically, it is only necessary that the known RI data storage part stores the types or degrees of polarities of stationary phases used when the retention indices of the registered substances were measured with classifying the types or degrees into four levels of non-polarity, low polarity, intermediate polarity, and high polarity; the receiving part receives which polarity of the four levels polarity of a stationary phase at the time of measuring an unknown sample has; and the RI data conversion part converts only registered substances having retention indices measured with use of stationary phases of which polarity levels are coincident. By doing so, only registered substances highly likely to coincide with the unknown sample can be converted to perform identification with high accuracy while reducing a load on an operation.

The known RI data storage part is not limited to one that stores only retention indices actually measured by gas chromatographic analysis under various conditions, but may be one that stores retention indices converted from known retention indices without making actual measurements as described in each of the embodiments. That is, retention indices converted in order to identify an unknown sample may be added to the known RI data storage part.

The present invention may be adapted to preliminarily calculate retention indices under a number of temperature conditions for each of a number of registered substances from pieces of known RI data; store them in the post-conversion RI data storage part with relating them to corresponding identifiers; and use the stored retention indices together with corresponding identifiers as a database.

Also, the data processing device for a gas chromatograph is not necessarily required to be provided together with the gas chromatograph. For example, the data processing device for a gas chromatograph may be used alone, and used in order to be inputted with a retention index obtained by gas chromatographic analysis under some temperature condition and convert to a retention index under another temperature condition.

The known RI data storage part may be one that is stored in a storage area inside a computer, or may be a library that is opened in academic organizations through, for example, the Internet or the like.

In addition, the data processing device for a gas chromatograph may be one that is configured to only include: a known RI data storage part that stores a plurality of pieces of known RI data each in which an identifier specific to each of registered substances, and retention indices actually measured by gas chromatographic analysis at a plurality of different temperatures on a registered substance indicated by the identifier are paired; and a known RI data conversion part that is configured to convert from the retention indices of the registered substance at the plurality of different temperatures to a retention index of the registered substance under a predetermined temperature condition for each of the pieces of known RI data. If so, for example, regarding an existing library of retention indices for which temperature conditions are not unified, the temperature conditions can be standardized. If there is such a library using a standardized temperature condition, in the case of performing gas chromatographic analysis, it is only necessary to perform an experiment at a standardized temperature. Also, the library may also be used to, with use of the retention index conversion method described in each of the above embodiments, convert a retention index of an unknown sample.

Further, regarding the known RI data conversion part, the respective configurations described in the above first, second, and third embodiment may be combined. That is, the present invention may be adapted to be able to appropriately select a conversion method from among the plurality of conversion methods to convert a retention index. Also, a program that realizes each of the above-described embodiments, or some functions may be installed in an existing data processing device for a gas chromatograph or computer by means of a recording medium that records the program.

Besides, the embodiments may be variously combined or modified without violating the scope of the present invention.

INDUSTRIAL APPLICABILITY

According to the present invention, a data processing device for a gas chromatograph that can identify an unknown sample by gas chromatographic analysis alone, which has been believed to be very difficult, can be provided.

The invention claimed is:

1. A data processing device for a gas chromatograph, comprising:
a known retention index data converter that is configured to receive pieces of retention index data for an identified substance indicating retention indices respectively at a plurality of mutually different temperatures that are identified, the retention indices being related with an identifier specific to the identified substance, and convert from the retention indices of the identified substance at the plurality of different temperatures to a retention index of the identified substance at a predetermined temperature condition,
wherein
the known retention index data converter is further configured to perform calculations; and
the calculations comprise:
a retention time conversion that converts from, retention indices of the identified substance at a first temperature and a second temperature that are two different temperatures, to an adjusted retention time of the identified substance under the predetermined temperature condition, and
a retention index calculation that calculates a retention index of the identified substance under the predetermined temperature condition on a basis of the adjusted retention time of the identified substance under the predetermined temperature condition.

2. The data processing device for a gas chromatograph according to claim 1, wherein:
the predetermined temperature condition is a condition including an isothermal analysis temperature that is appropriately set when gas chromatographic analysis is performed as isothermal analysis; and
the calculations are performed on a basis of retention indices of the identified substance at a first temperature and a second temperature that are two different temperatures, and adjusted retention times of a reference substance at the first temperature, the second temperature, and the isothermal analysis temperature.

3. The data processing device for a gas chromatograph according to claim 1, wherein
the known retention index data converter comprises:
a known temperature retention time converter that, on a basis of retention times of the reference substance at the first temperature and the second temperature, converts from the retention indices of the identified substance at the first temperature and the second temperature to adjusted retention times of the identified substance at the first temperature and the second temperature;
an isothermal analysis temperature retention time calculator that, on a basis of a linear relationship between reciprocals of the first temperature and the second temperature, and logarithms of the adjusted retention times of the identified substance, the adjusted retention times corresponding to the first and second temperatures, calculates an adjusted retention time of the identified substance at the isothermal analysis temperature; and
an retention index calculator that, on a basis of the adjusted retention time of the identified substance at the isothermal analysis temperature, and the adjusted retention time of the reference substance at the isothermal analysis temperature, calculates the retention index of the identified substance at the isothermal analysis temperature.

4. The data processing device for a gas chromatograph according to claim 1, wherein
the predetermined temperature condition is a condition including an isothermal analysis temperature that is appropriately set when gas chromatographic analysis is performed as isothermal analysis, and
the known retention index data converter further comprising:
an retention index temperature function identifier that, on a basis of retention indices of the identified substance at a first temperature, a second temperature, and a third temperature that are three different temperatures, identifies three constants of a conversion expression that is a function of temperature as provided below:

$$I = A + \frac{B}{T} + C\ln T$$

where I: the retention index, T: temperature, and A, B, and C: the constants identified by measured values of retention indices of each identified substance; and a temperature substitution operator that substitutes the isothermal analysis temperature into the conversion expression identified by the retention index temperature function identifier to calculate a retention index of the identified substance at the isothermal analysis temperature.

5. The data processing device for a gas chromatograph according to claim 1,
wherein
the predetermined temperature condition is a condition including a temperature rising condition including: a temperature rising rate and an initial setting temperature that are appropriately set when gas chromatographic analysis is performed as temperature rising analysis, and
the known retention index data converter comprising:
a distribution coefficient function identifier that, on a basis of retention indices of the identified substance at a first temperature and a second temperature that are two different temperatures, identifies a distribution coefficient of the identified substance as a function of temperature;
a temperature rising condition retention time calculator that, on a basis of the distribution coefficient and a column length of a gas chromatograph, calculates an adjusted retention time of the identified substance under the temperature rising condition; and
a temperature rising condition retention index calculator that, on a basis of the adjusted retention time of the identified substance under the temperature rising condition, and an adjusted retention time of a reference substance under the temperature rising condition, calculates a retention index of the identified substance under the temperature rising condition.

6. A data processing device for a gas chromatograph, comprising:
a known retention index data converter that is configured to receive pieces of known retention index data indicating retention indices respectively at a plurality of mutually different temperatures, the retention indices being related with an identifier specific to an identified substance, and convert from the retention indices of the identified substance at the plurality of different temperatures to a retention index of the identified substance at a predetermined temperature condition;
a known retention index data storage that stores known retention index data on each of a plurality of identified substances;
a post-conversion retention index data storage that stores retention indices of at least of identified substances with corresponding specific identifiers to the retention indices, the retention indices being converted by the known retention index data converter;
a receiver that receives the predetermined temperature condition, and a value related to a retention index of an unknown sample measured by gas chromatographic analysis using the predetermined temperature condition; and
a searcher that:
extracts, from among pieces of post-conversion retention index data stored in the post-conversion retention index data storage, post-conversion retention index data including a retention index of which a value is coincident with or substantially equal to a value of the retention index of the unknown sample under the predetermined temperature condition, the retention index of the unknown sample being received by the receiver, and outputs an identifier corresponding to the extracted retention index, or
extracts, from among pieces of post-conversion retention index data stored in the post-conversion retention index data storage, a plurality of identifiers respectively having retention indices that are within a predetermined range with respect to the value of the retention index of the unknown sample under the predetermined temperature condition, to prepare candidate sets, the retention index of the unknown sample being received by the receiver, and outputs an identifier common to the respective candidate sets prepared on a basis of the respective combinations each including the predetermined temperature condition and the retention index.

7. The data processing device for a gas chromatograph according to claim 6, wherein
the known retention index data converter is configured to convert, from among the retention indices of the identified substance at the plurality of different temperatures, the retention indices being stored in the retention index data storage, a retention index having a value within a predetermined range with respect to the value of the retention index of the unknown sample, the value being received by the receiving, to the retention index of the identified substance under the predetermined temperature condition.

8. A non-transitory computer readable medium comprising a data processing program for a gas chromatograph, the data processing program, when executed by a processor, causing a computer to perform a process comprising: receiving, at a known retention index data converter, pieces of known retention index data indicating retention indices respectively at a plurality of mutually different temperatures from a known retention index data storage that stores known retention index data for each of a plurality of identified substances, the retention indices being related with an identifier specific to some identified substance, and convert from the retention indices of the identified substance at the plurality of different temperatures to a retention index of the identified substance under a predetermined temperature condition,
wherein
the known retention index data converter is configured to perform calculations; and
the calculations comprise:
a retention time conversion that converts from, retention indices of the identified substance at a first temperature and a second temperature that are two different temperatures, to an adjusted retention time of the identified substance under the predetermined temperature condition, and
a retention index calculation that calculates a retention index of the identified substance under the predetermined temperature condition on a basis of the adjusted retention time of the identified substance under the predetermined temperature condition.

9. A data processing method for a gas chromatograph, comprising:
receiving retention indices respectively at a plurality of mutually different temperatures, the retention indices being related with an identifier specific to each identified substance from a known retention index data storage that stores known retention index data for each of a plurality of identified substances; and converting from the retention indices of the identified substance at the plurality of different temperatures to a retention index of the identified substance at a predetermined temperature condition,
wherein
the converting comprises:
converting from retention indices of the identified substance at a first temperature and a second temperature that are two different temperatures to adjusted retention time of the identified substance under the predetermined temperature condition, and
calculating a retention index of the identified substance under the predetermined temperature condition on a basis of the adjusted retention time of the identified substance under the predetermined temperature condition.

10. A database for a gas chromatograph, comprising a post-conversion retention index data storage that stores a retention index of each identified substance, the retention index being converted by the data processing method for a gas chromatograph according to claim 9.

\* \* \* \* \*

UNITED STATES PATENT AND TRADEMARK OFFICE
CERTIFICATE OF CORRECTION

PATENT NO.         : 9,222,923 B2                                           Page 1 of 1
APPLICATION NO.    : 14/197635
DATED              : December 29, 2015
INVENTOR(S)        : T. Sasaki et al.

It is certified that error appears in the above-identified patent and that said Letters Patent is hereby corrected as shown below:

Title Page/Other Publications, page 2, column 2, line 5, please change "Eurpean Search" to
-- European Search --

Claims

Column 22, line 41 (claim 3, line 19) please change "an retention" to -- a retention --

Column 22, line 56 (claim 4, line 9) please change "an retention" to -- a retention --

Signed and Sealed this
Seventh Day of June, 2016

Michelle K. Lee
*Director of the United States Patent and Trademark Office*